United States Patent [19]
Pavlo et al.

[11] Patent Number: 5,824,000
[45] Date of Patent: Oct. 20, 1998

[54] PRESSURE INFUSER APPARATUS

[76] Inventors: John A. Pavlo, 1930 Temple Ter., Clearwater, Fla. 34624; Hiroaki Watanabe, 5-36 2-chome, Nakanoshima, Saiki-City Oita-Pref., Japan; Makoto Hirao, 2098-1 Oaza Nakahara, One-Machi, One-Gun Oita-Pref., Japan; Masato Okubo, 2-7-15 Minami-Rokugo, Ota-Ku, Tokyo, Japan

[21] Appl. No.: 210,907

[22] Filed: Mar. 21, 1994

[51] Int. Cl.⁶ .................................................. A61M 5/148
[52] U.S. Cl. ........................................ 604/142; 604/153
[58] Field of Search .................................. 604/153, 141, 604/142, 132; 128/DIG. 12; 73/729.1

[56] References Cited

U.S. PATENT DOCUMENTS

| | | | |
|---|---|---|---|
| 1,482,947 | 2/1924 | Shorts | 73/729.1 |
| 1,946,224 | 2/1934 | Mastrangel | 73/729.1 |
| 2,689,481 | 9/1954 | Quiat | 73/729.1 |
| 3,055,219 | 9/1962 | Wilson et al. | 73/729.1 |
| 3,238,781 | 3/1966 | Peters | 73/729.1 |
| 3,895,741 | 7/1975 | Nugent | 604/141 |
| 4,090,514 | 5/1978 | Hinck et al. | 604/142 |
| 4,507,116 | 3/1985 | Leibinsohn | 604/142 |
| 4,613,327 | 9/1986 | Tegrarian et al. | 128/DIG. 12 |
| 4,684,367 | 8/1987 | Schaffer et al. | 128/DIG. 12 |
| 4,735,613 | 4/1988 | Bellin et al. | 604/142 |
| 5,053,011 | 10/1991 | Strobel | 604/142 |
| 5,059,182 | 10/1991 | Laing | 604/142 |
| 5,071,104 | 12/1991 | Witt et al. | 604/142 |
| 5,125,900 | 6/1992 | Teves | 604/142 |

*Primary Examiner*—Paul J. Hirsch

[57] ABSTRACT

An apparatus for supporting a flexible bag containing fluid and for applying pressure to the bag to thereby facilitate the dispensing of the fluid from the bag, comprising a cuff adapted to support a bag of fluid to be dispensed and to apply pressure to facilitate the dispensing of the fluid; A gauge to determine and display the pressure within the cuff, the gauge being formed of a housing with a fluid port; and a manifold having a passageway in fluid communication with the cuff, a passageway in fluid communication with a pump for inflating the cuff, and a passageway coupled with respect to the gauge.

6 Claims, 7 Drawing Sheets

PRESSURE INFUSER APPARATUS

BACKGROUND OF THE INVENTION

1. Summary of the Invention

This invention relates to pressure infuser apparatus and, more particularly, to apparatus for supporting a flexible I.V. bag containing fluid and for applying pressure to the bag to thereby facilitate the dispensing of the fluid from the bag, the apparatus comprising in combination a cuff adapted to support a bag of fluid to be dispensed and to apply pressure to facilitate the dispensing of the fluid; a gauge to determine and display the pressure within the cuff, the gauge being formed of a housing with a fluid port; and a manifold having a passageway in fluid communication with the cuff, a passageway in fluid communication with a pump for inflating the cuff, and a passageway coupled to the gauge.

2. Summary of the Background Art

In the medical arts, it is common to administer intravenous liquids to a patient. Such liquids, which may be dextrose or saline solutions, whole blood, plasma, or the like, are normally contained in a flexible, transparent I.V. bag. The bag is supported above the patient and a tubing or line couples the bag with a needle so that the liquid from the bag may gravity flow into the patient through the needle by the action of gravity.

One advance in the arts is pressure infusion apparatus. Pressure infusion apparatus normally takes the form of an inflatable member in contact with the bag. A ball pump inflates the inflatable member to apply a pressure to the bag for enhancing the flow of the liquid from the bag into the patient. Such application of pressure is desirable, particularly as the liquid becomes more depleted from the bag. A more recent advance in the field of pressure infusion apparatus and devices is the gauge for determining the pressure within the cuff. Earlier gauges were of the rotary dial type, expensive and difficult to read. Later gauges involved a plunger reciprocable within a fixed tube. The greater the pressure, the further the plunger would extend from the tube. Such tube/plunger arrangements were either positioned directly through the wall of the cuff or in the line from the ball pump to the cuff. In any event, tube/plunger arrangements required cuffs of more complex constructions or special lines in order to accommodate the gauges.

Typical devices for these purposes are disclosed in the patent literature. Consider for example U.S. Pat. No. 4,735,613 to Bellis and U.S. Pat. No. 5,053,012 to Edwards. According to the Bellis disclosure, a pressure infusion apparatus is formed of an inflatable member and an in-extensible mesh with an I.V. bag therebetween. A gauge of the tube/plunger type extends through a wall of the inflatable member. There is no teaching or suggestion of inflatable components on both sides of the I.V. bag and an accordion-shaped member or bellows as a functioning element of a gauge or a manifold for simplified coupling of the gauge with respect to the cuff.

According to the Edwards disclosure, a pressure infusion apparatus is formed of an inflatable member and a transparent sheet with an I.V. bag therebetween. A gauge of the tube/plunger type either extends through a wall of the inflatable member or is in line with the line coupling the cuff with the ball pump. There is no teaching or suggestion of inflatable components on both sides of the I.V. bag, a bellows as a functioning element of a gauge or a manifold for simplified coupling of the gauge with respect to the cuff.

Accordingly, it is an object of the present invention to provide an improved apparatus for supporting a flexible bag containing fluid and for applying pressure to the bag to thereby facilitate the dispensing of the fluid from the bag, the apparatus comprising, in combination, a cuff adapted to support a bag of fluid to be dispensed and to apply pressure to facilitate the dispensing of the fluid; a gauge to determine and display the pressure within the cuff, the gauge being formed of a housing with a fluid port; and a manifold having a passageway in fluid communication with the cuff, a passageway in fluid communication with a pump for inflating the cuff, and a passageway coupled with respect to the gauge.

It is a further object of the present invention to simplify the use of pressure infusion apparatus.

It is a further object of the present invention to reduce the cost of pressure infusion apparatus.

It is a further object of the present invention to encompass an I.V. bag with a cuff of a pressure infusion apparatus wherein the cuff is formed of elastic material which expands greater on the side adjacent to the bag than remote therefrom.

It is a further object of the present invention to utilize a bellows as the expansion member of a gauge.

Lastly, it is an object of the present invention to couple a cuff, pump and gauge through a manifold to simplify the intercoupling of the functioning components of a pressure infusion apparatus.

The foregoing has outlined some of the more pertinent objects of the invention. These objects should be construed to be merely illustrative of some of the more prominent features and applications of the intended invention. Many other beneficial results can be obtained by applying the disclosed invention in a different manner or modifying the invention within the scope of the disclosure. Accordingly, other objects and a fuller understanding of the invention and the detailed description of the preferred embodiment in addition to the scope of the invention defined by the claims taken in conjunction with the accompanying drawings.

SUMMARY OF THE INVENTION

The invention is defined by the appended claims with specific embodiments shown on the attached drawings. For the purpose of summarizing this invention, the invention may be incorporated into an improved pressure infuser apparatus for supporting a flexible bag containing fluid and for applying pressure to the bag to thereby facilitate the dispensing of the fluid from the bag, the apparatus comprising, in combination, a cuff formed of an inner sheet and a superposed outer sheet, each sheet being of a generally rectangular configuration with longer, parallel, horizontal upper and lower edges and with shorter, parallel, vertical side edges extending between the upper and lower edges, the cuff being bendable about a vertical fold line intermediate the side edges, the sheets being fabricated of a flexible fluid-impervious material, all the edges having RF sealed lines around the periphery of the sheets to define an air chamber between the sheets and with additional RF sealed lines coupling the sheets to preclude excess ballooning of the cuff when inflated, the inner sheet being more elastic than the outer sheet to expand greater inwardly toward a supported bag than outwardly when the cuff is inflated; a support plate with a lower extent RF coupled to the inner sheet adjacent to the upper edge between the fold line and one side edge, the lower extent having a hook coupled to the sheets for supporting a bag, the support plate also having an upper extent with a hole for supporting the cuff; a strap with a first end RF coupled to the outer sheet adjacent to one side edge and a second end laterally spaced therefrom, the strap being of a length to encompass the cuff when folded with a bag supported interior thereof, pile-type fasteners secured to the first and second ends of the strap for releasably coupling the ends of the strap when supporting a bag; a gauge to determine and display the pressure within the cuff, the gauge being formed of a housing, the housing having a lower portion with a fluid port adjacent to the bottom thereof, the housing having a central transparent portion, and the housing having an upper portion defining a chamber within the housing, a cup-shaped member located within the chamber, a normally collapsed accordion-shaped member located between the fluid port and the cup-shaped member adapted to expand and raise the cup-shaped member upon the introduction of air into the gauge, a coil spring located between the cup-shaped member against the expansion of the accordion-shaped member, indicia on the surface of the cup-shaped member adapted to be read by an operator through the central portion as a function of the pressure within the cuff as sensed by the gauge, and a support member extending from the upper end of the gauge for coupling to the cuff; and a manifold having an upwardly extending passageway in fluid communication with the interior of the cuff, a downwardly extending passageway in fluid communication with a squeeze ball for inflating the cuff, an outwardly extending passageway with a sealing cap coupled by a friction fitting of the tapered Luer type for the quick release of the cap to effect emergency deflation of the cuff, and a supplemental passageway extending upwardly from the outwardly extending passageway coupled to the accordion-shaped member and in fluid communication therewith and to assist in the securement of the gauge with respect to the cuff.

The invention may also be incorporated into an improved cuff, gauge, or manifold for pressure infusion apparatus.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent structures do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which.

Similar reference characters refer to similar parts throughout the several views of the drawings.

DETAILED DESCRIPTION OF THE PREFERRED EMBODIMENT

Figure 1:
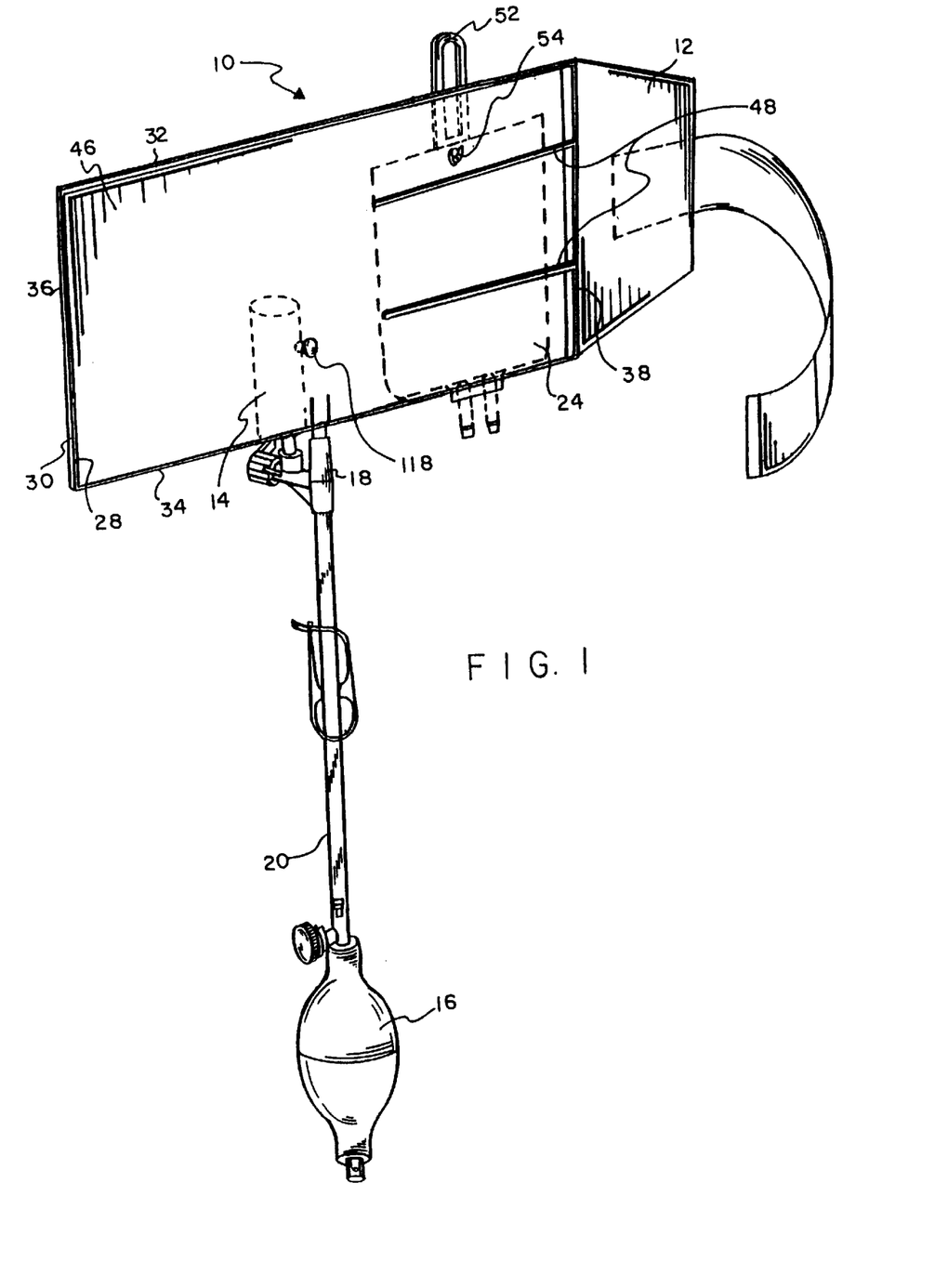
FIG. 1 is a perspective illustration of pressure infusing apparatus constructed in accordance with the principles of the present invention and showing in dotted lines a bag of liquid to be dispensed.

Shown in the Figures, with particular reference to FIG. 1, is a pressure infuser apparatus 10. The apparatus includes a cuff 12, a gauge 14, a ball pump 16 and a manifold 18 with passageways and tubing 20 operatively coupling the pump and manifold in a system configuration. The apparatus is adapted to support a flexible, transparent I.V. bag 24 containing fluid such as dextrose or saline solutions, whole blood, plasma, or the like. A line is fed through the bottom of the bag to a needle which is inserted into the patient for administration to the patient. Flow to the patient is through the action of gravity.

Figure 2:
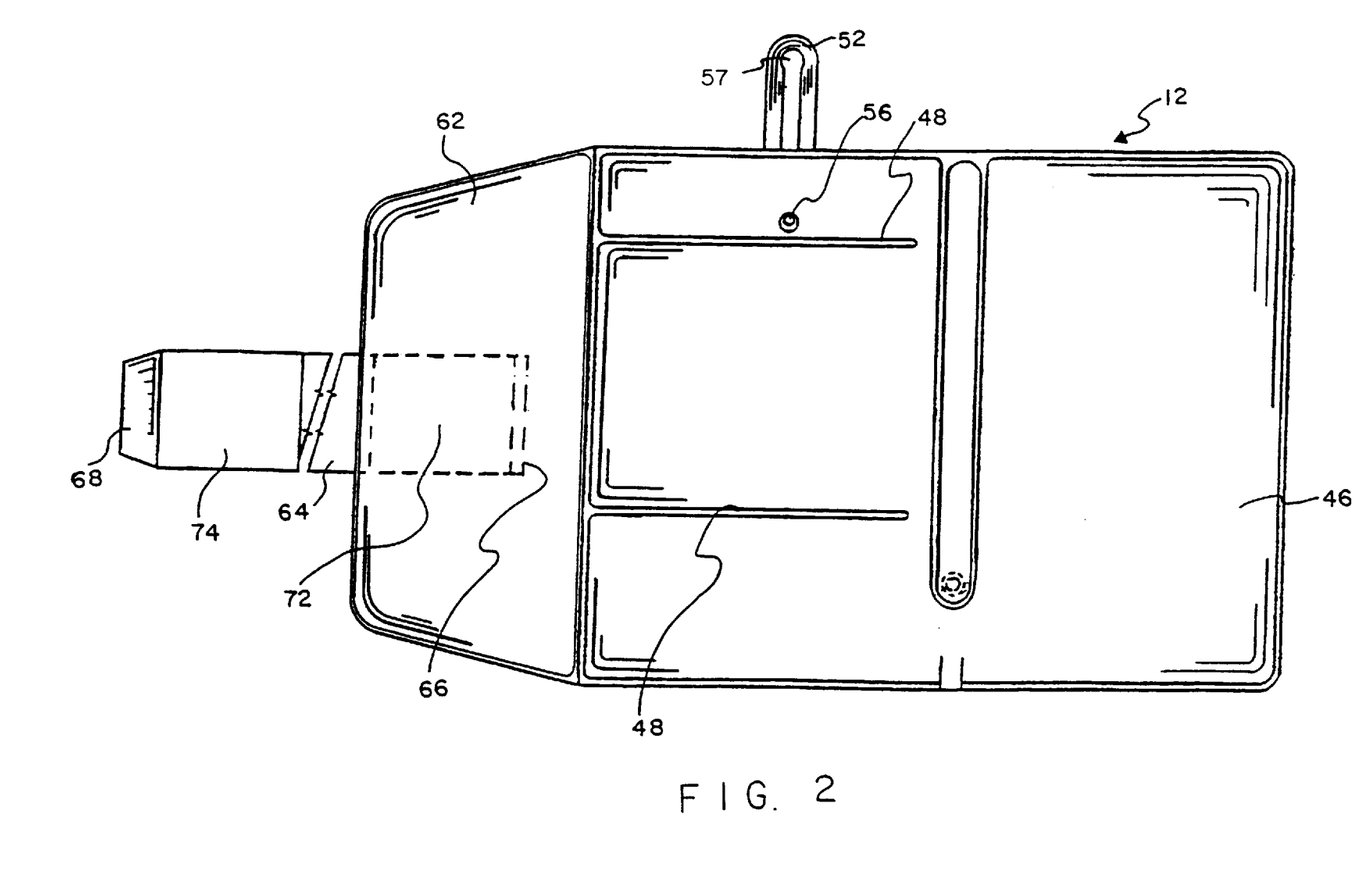
FIG. 2 is a plan view of the cuff of the pressure infusing apparatus of FIG. 1.

A cuff 12 is part of the apparatus and functions for applying pressure to the bag 24 so as to facilitate the dispensing of the fluid from the bag. The cuff is formed of an inner sheet 28 and a superposed outer sheet 30. The sheets are shaped in a generally rectangular configuration with longer, parallel, horizontal upper and lower edges 32 and 34 and with shorter, parallel, vertical side edges 36 and 38 which extend between the upper and lower edges. The cuff if fabricated of a transparent, flexible, fluid-impervious, elastic material, preferably a polymer, such as for example, polyvinyl chloride (PVC) or polyurethanes. The sheets and cuff are bendable about a vertical fold line 42 intermediate the side edges. All the edges have RF sealed lines 44 around the periphery of the sheets to define an air chamber 46 between the sheets. Additional RF sealed lines 48 couple the sheets to preclude excess ballooning of the cuff when inflated. In the preferred mode of the invention, the inner sheet 28 is thinner and, consequently, more elastic than the outer sheet 30. This allows the inner sheet to expand greater inwardly toward a supported bag than outwardly when the cuff is inflated. The inner sheet is preferably about 0.004 inches thick while the outer sheet is preferably about 0.008 inches thick, plus or minus 10 percent.

Coupled to the inner sheet is a support plate 52. The support plate has its lower extent coupled as by radio frequency (RF) waves to the sheets adjacent to the upper edge 36 between the fold line 42 and one side edge 38. The lower end of the plate has a hook 54 for supporting an I.V. bag. The support plate also has an upper extent with a hole 57 for receiving a hook 58 of a conventional stand, not shown, from which the pressure infusion apparatus is supported above the patient in the conventional manner.

The cuff has formed from the sheets from which it is formed, a tapering lateral extension 62. Extending laterally from the extension is a strap 64 with a first end 66 RF coupled to the outer sheet adjacent to one side edge. A second end 68 of the strap is laterally spaced therefrom. The strap is of a length to encompass the cuff when folded while a bag supported interior thereof. Pile-type fasteners 72 and 74 such as velcro is secured to the first and second ends of the strap on opposite sides thereof for releasably coupling the ends of the strap when supporting a bag.

Figure 4:
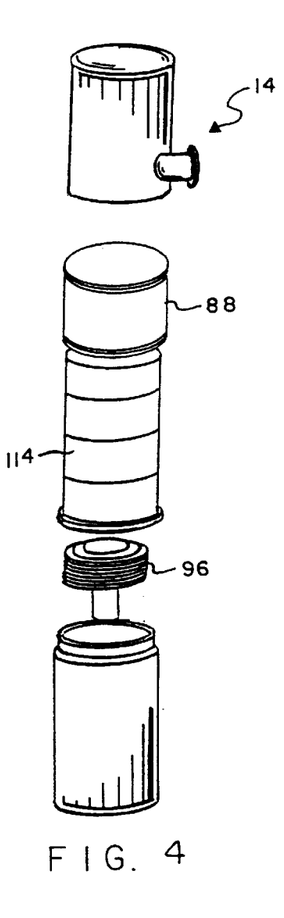
Figure 5:
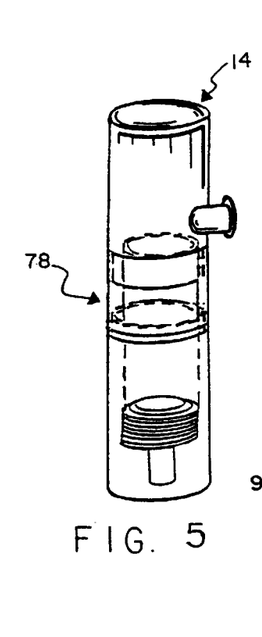
FIGS. 5, 6 and 7 are perspective showings of the gauge of FIGS. 1, 3 and 4 illustrating various different pressures being sensed.
Figure 6:
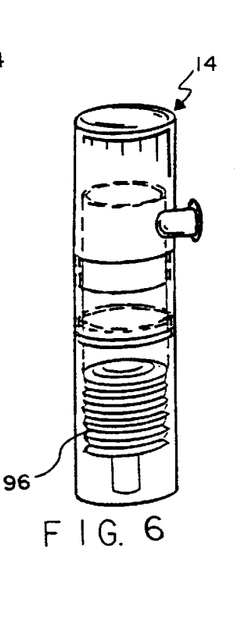
Figure 7:
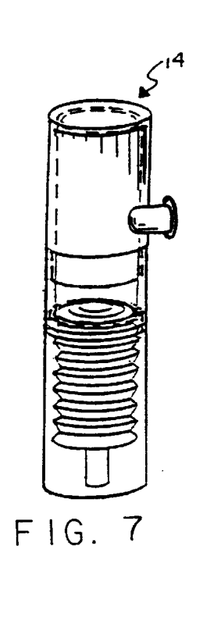

In order to determine and display the pressure within the cuff, a gauge 14 is provided. Note FIGS. 3 through 8. The gauge is preferably formed of an exterior cylindrical housing 78. The housing has a lower portion 80 with a fluid port 83 adjacent to its bottom wall 84. The housing also has a central cylindrical transparent portion 88 through which the pressure within the cuff may be displayed and read from any angle. Lastly, the housing has an upper portion 90. When coupled, a cylindrical chamber 92 is defined within the housing. A cup-shaped member 94 is located within the chamber adjacent to the central extent. Adjacent to the lower extent of the chamber is a normally collapsed bellows or accordion-shaped member 96. The accordion-shaped member is located between the fluid port and the cup-shaped member adapted to expand and raise the cup-shaped member upwardly upon the introduction of air into the gauge. Also within the chamber is a coil spring 98 located between the cup-shaped member and the upper portion. The spring is adapted to urge the cup-shaped member downwardly against the expansion of the accordion-shaped member. A downwardly extending cylindrical extension 102 projects downwardly from the top surface of the upper portion to receive the upper part of the spring and preclude its buckling. The lower part of the spring contacts the lower surface of the cup-shaped member. The lower part of the spring is located in a cylindrical recess formed by an upwardly extending projection formed in the cup-shaped member. Continuing expansion of the accordion-shaped member by increasing pressure in the cuff is illustrated by FIGS. 5, 6 and 7. Coupling of the upper and lower portions and the transparent portion is effected by a circular recess 108 formed exteriorly in the surface of the transparent portion 88 adjacent to its ends. Such recesses cooperate to receive circular projections 110 at the adjacent ends of the upper and lower portions of the housing. Such an arrangement allows for simple snap coupling and uncoupling of the housing portions.

To facilitate the display and reading of the pressure within the cuff, a strip 114 is adhered as by glue to the cup-shaped member. Note FIG. 3. Indicia, information bearing material, is printed on the surface of the sheet. The indicia preferably takes the form of numbers, such as 150, 300, or the like representing the pressure in millimeters of mercury within the cuff. In addition, the indicia numbers are preferably supplemented by indicia colors in circular bands, three to five in the disclosed preferred embodiment, representing the numbers and, hence, the pressure. The indicia is adapted to be read by an operator through the central transparent portion as a function of the pressure within the cuff as sensed by the gauge.

Figure 3:
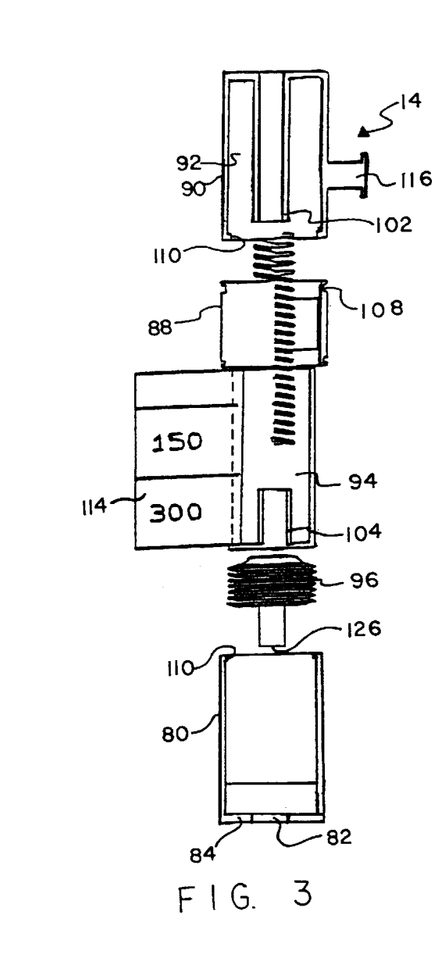
FIGS. 3 and 4 are exploded views, in section and in perspective, of the gauge as shown in FIG. 1.

It is preferred to include a red warning strip 113 at an intermediate portion of the strip 114 for a quick indication that pressure in the cuff is increasing as the ball pump 16 is squeezed. A second red indicator strip 115 is at the lower extent of the strip 114 as a warning of excess pressure in the cuff requiring appropriate pressure relief.

The pressure to which the cuff is to be inflated is a function of the particular application, the treatment to be provided to the patient by the doctor or other health care giver. If, for example, a patient has lost a significant amount of blood and a rapid blood transfusion is needed, then the pressure in the cuff might be 300 millimeters of mercury.

The gauge also includes a support member in the form of a button 116 extending radially outwardly from adjacent to the upper end of the gauge for coupling to the cuff through a hole 118 extending through both sheets of the cuff. The hole is RF heat sealed around its periphery in order to preclude the leakage of air from the cuff during operation and use.

Figure 8:
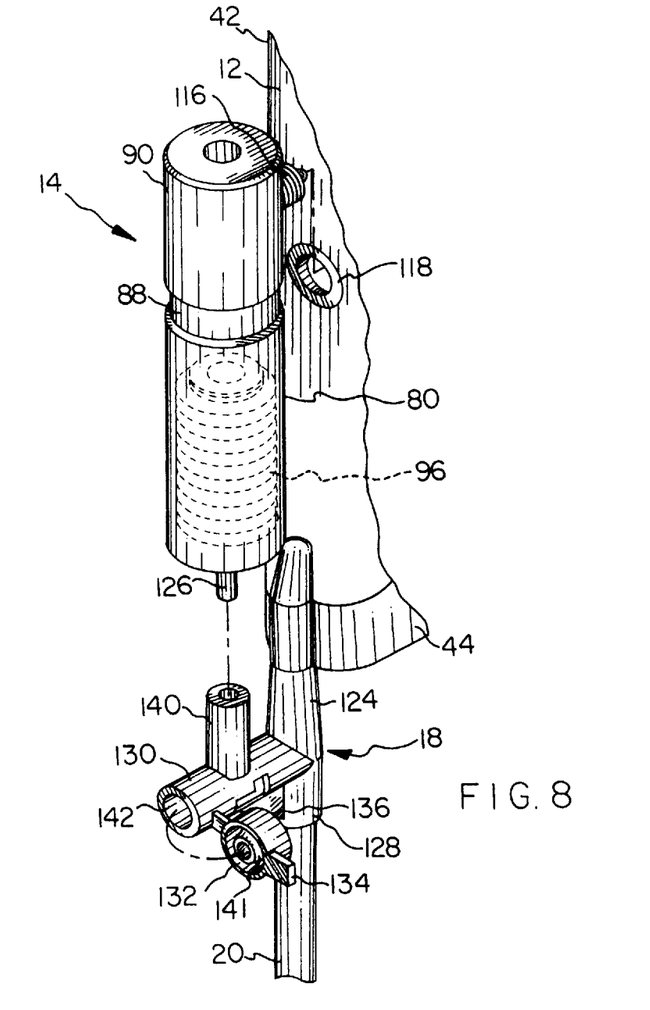
FIG. 8 is an exploded perspective view of the gauge and associated components of the apparatus shown in FIGS. 1 and 2.
Figure 9:
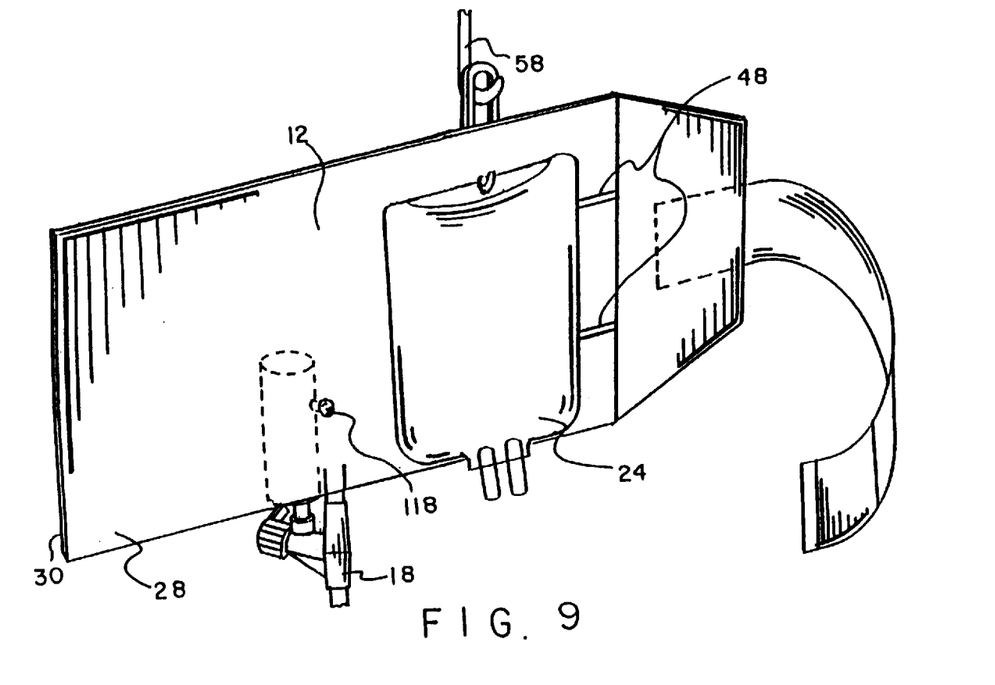
FIGS. 9 through 13 illustrate a liquid-containing I.V. bag being supported by the pressure infusing apparatus of the present invention and the apparatus being wrapped around the bag in anticipation of operation and use.
Figure 10:
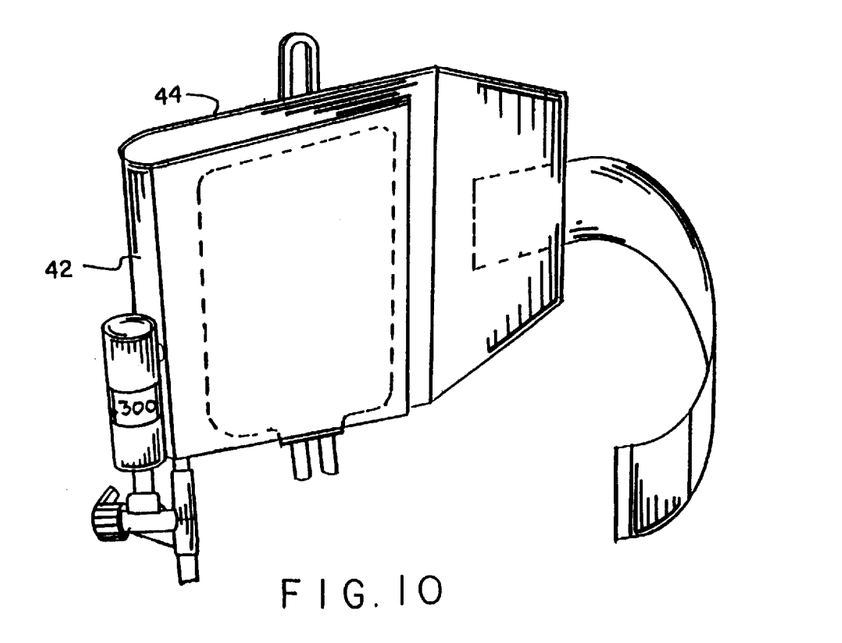
Figures 11, 12, 13:
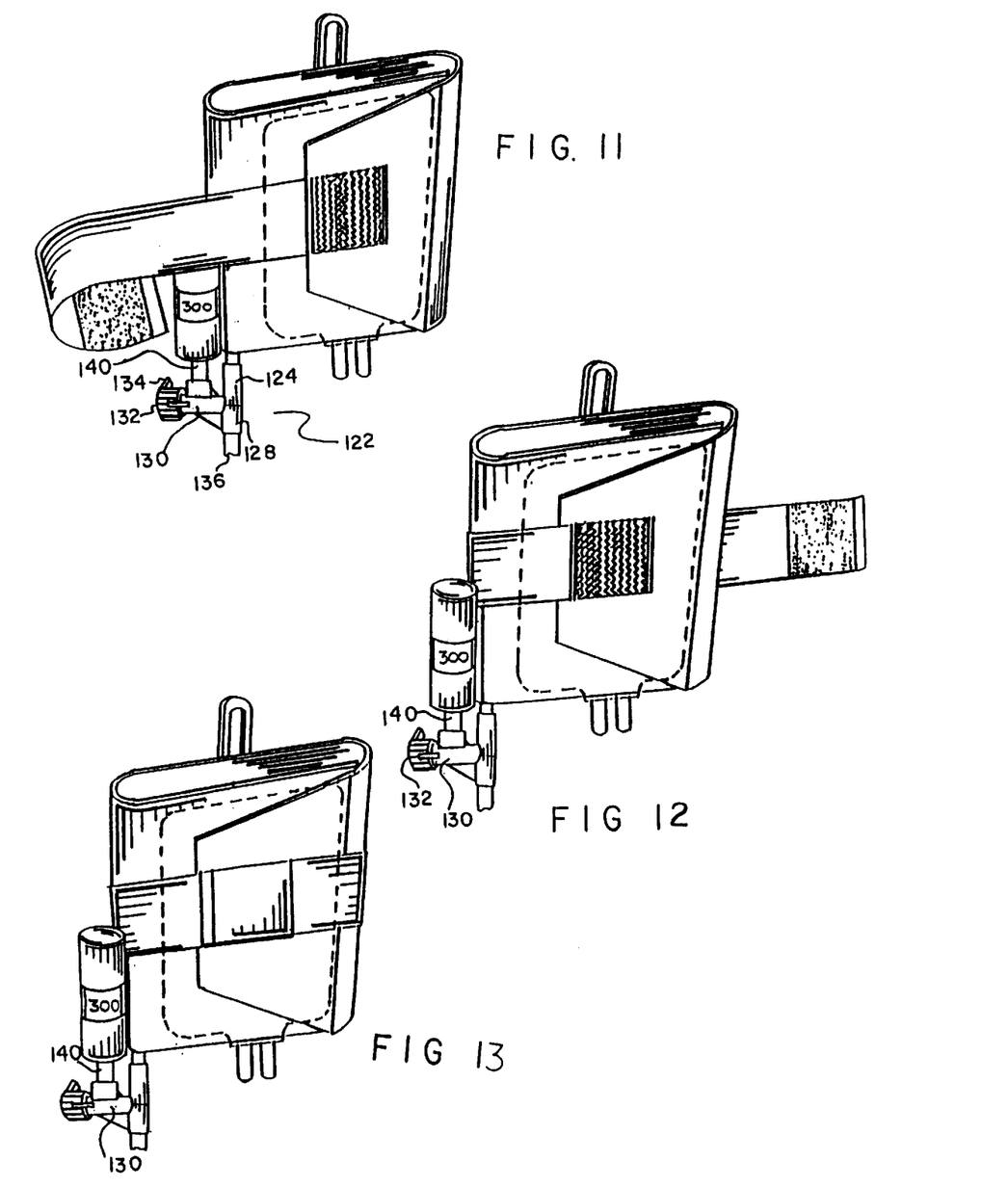
Figure 14:
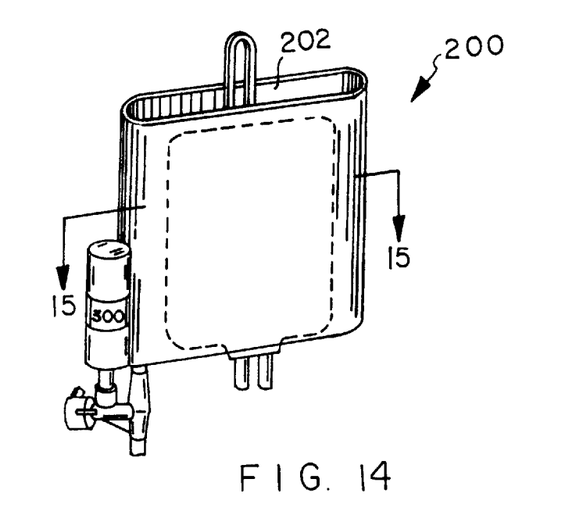
FIGS. 14 and 15 illustrate a pressure infusion apparatus in a cylindrical configuration constructed in accordance with an alternate embodiment of the invention.
Figure 15:
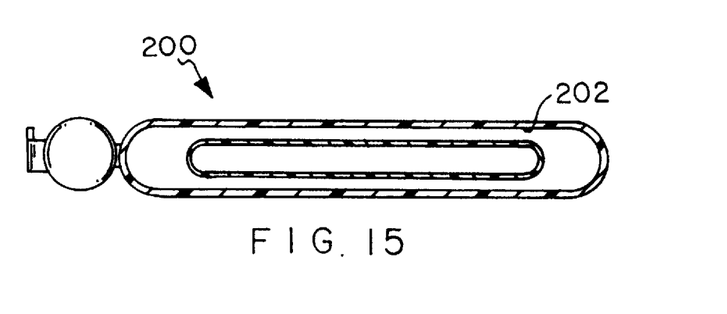

Coupling the cuff, gauge and squeeze ball pump is a manifold 18. The manifold has an upwardly extending passageway 124 in fluid communication with the interior of the cuff through its aperture 126, a downwardly extending passageway 128 with a tubing or line 20 in fluid communication with the squeeze ball for inflating the cuff, and an outwardly extending passageway 130 with a sealing cap 132 press coupled through a friction Luer or tapered fitting for the quick release of the cap to effect emergency deflation of the cuff. A projection 134 on the cap allows for a quick separation of the cap from the manifold. A connector strap 136 couples the cap and manifold to preclude losing the cap. A supplemental passageway 140 extends upwardly from the outwardly extending passageway for insertion into, and coupling with, the lower aperture 126 of the accordion-shaped member. The accordion-shaped member is, therefore, in fluid communication with the cuff and ball pump for proper reading of the cuff pressure and to assist in the securement of the gauge, at its lower end, with respect to the cuff.

Note is taken that the upper end of the gauge 14 is coupled to the cuff 12 by the button 116 through hole 118 in the cuff. The lower end of the gauge is coupled to the cuff through the coupling of the bellows 96 with the manifold 18. In this manner, the gauge is held in a readable orientation, vertically oriented parallel with the fold line of the cuff but slight spaced therefrom.

The apparatus of the present invention may be constructed in virtually any size as a function of the particular application. Such sizes would referably include sizes to accommodate the more conventional half liter (500 milliliter), one liter (1,000 milliliter), two liters (2,000 milliliter), three liters (3,000 milliliter), etc. While it is preferred that a specific apparatus be specifically selected for a particularly sized bag, it has been found that an apparatus may accommodate the particularly sized bag as well as the next smaller bag.

In operation and use, the pressure infusion apparatus of the present invention is suspended by a hook of a conventional I.V. stand, not shown, at a location above the patient to receive the contents of an I.V. bag intravenously. The I.V. bag is then suspended from the hook coupled to the sheets of the cuff. Note FIG. 8 as well as FIGS. 9 through 12. The I.V. bag is in contact with the first half of the cuff. The second half of the cuff, that remote from the bag, is then folded over at the fold line to encompass the bag with the inner sheet of the cuff with the higher coefficient of elasticity in contact with the bag. The uninflatable extension of the sheets is then folded over the second half of the cuff. The strap is then wrapped around the cuff with its second or distal end releasably coupling with the first or proximal end. The pressure infusion apparatus is now ready to be deployed by coupling the contents of the I.V. bag to the patient through the line and needle. Thereafter pressure is applied to the bag by the inflation of the cuff by the squeeze ball pump. Reading of the gauge is continued until the desire pressure is displayed and read. Thereafter a conventional clip on the tubing or line above the pump is engaged to preclude the undesired relieving of the pressure from the cuff.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,
What is claimed is:

1. Pressure infuser apparatus for supporting a flexible bag containing fluid and for applying pressure to the bag to thereby facilitate the dispensing of the fluid from the bag, the apparatus comprising, in combination:

a cuff formed of an inner sheet and a superposed outer sheet, each sheet being of a generally rectangular configuration with longer, parallel, horizontal upper and lower edges and with shorter, parallel, vertical side edges extending between the upper and lower edges, the cuff being bendable about a vertical fold line intermediate the side edges, the sheets being fabricated of a flexible fluid-impervious material, all the edges having RF sealed lines around the periphery of the sheets to define an air chamber between the sheets and with additional RF sealed lines coupling the sheets to preclude excess ballooning of the cuff when inflated, the inner sheet being more elastic than the outer sheet to expand greater inwardly toward a supported bag than outwardly when the cuff is inflated;

a support plate with a lower extent RF coupled to the sheets adjacent to the upper edge between the fold line and one side edge, the lower extent having a hook coupled to the sheets for supporting a bag, the support plate also having an upper extent with a hole for supporting the cuff;

a strap with a first end RF coupled to the outer sheet adjacent to one side edge and a second end laterally spaced therefrom, the strap being of a length to encompass the cuff when folded with a bag supported interior thereof, pile-type fasteners secured to the first and second ends of the strap for releasably coupling the ends of the strap when supporting a bag;

a gauge to determine and display the pressure within the cuff, the gauge being formed of a housing, the housing having a lower portion with a fluid port adjacent to the bottom thereof, the housing having a central transparent portion, and the housing having an upper portion defining a chamber within the housing, a cup-shaped member located within the chamber, a normally collapsed accordion-shaped member located between the fluid port and the cup-shaped member adapted to expand and raise the cup-shaped member upon the introduction of air into the gauge, a coil spring located between the cup-shaped member against the expansion of the accordion-shaped member, indicia on the surface of the cup-shaped member adapted to be read by an operator through the central portion as a function of the pressure within the cuff as sensed by the gauge, and a support member extending from the upper end of the gauge for coupling to the cuff; and a manifold having an upwardly extending passageway in fluid communication with the interior of the cuff, a downwardly extending passageway in fluid communication with a squeeze ball for inflating the cuff, an outwardly extending passageway with a sealing cap coupled by a friction fitting for the quick release of the cap to effect emergency deflation of the cuff, and a supplemental passageway extending upwardly from the outwardly extending passageway coupled to the accordion-shaped member and in fluid communication therewith and to assist in the securement of the gauge with respect to the cuff.

2. An apparatus for supporting a flexible bag containing fluid and for applying pressure to the bag to thereby facilitate the dispensing of the fluid from the bag, the apparatus comprising:

a cuff adapted to support a bag of fluid to be dispensed and to apply pressure to facilitate the dispensing of the fluid, the cuff including a vertically disposed planar member foldable adjacent to the vertical mid-line thereof to form an interior region for receiving a flexible bag containing fluid, with the height of the cuff being greater than the height of the bag and the width of the cuff being greater than twice the width of the bag and further including a narrow strap coupled with respect to one vertical edge of the inflatable member and adapted to loop entirely around the folded container at a central extent thereof;

a gauge to determine and display the pressure within the cuff, the gauge being formed of a housing with a fluid port; and a manifold having a passageway in fluid communication with the cuff, a passageway in fluid communication with a pump for inflating the cuff, and a passageway coupled with respect to the gauge.

3. An apparatus for supporting a flexible bag containing fluid and for applying pressure to the bag to thereby facilitate the dispensing of the fluid from the bag, the apparatus comprising:

a cuff adapted to support a bag of fluid to be dispensed and to apply pressure to facilitate the dispensing of the fluid, the cuff having an inner sheet and a superposed outer sheet, each sheet being of a generally rectangular configuration with longer, parallel, horizontal upper and lower edges and with shorter, parallel, vertical side edges extending between the upper and lower edges, the cuff being bendable about a vertical fold line intermediate the side edges, the sheets being fabricated of a flexible fluid-impervious material, all the edges having RF sealed lines around the periphery of the sheets to define an air chamber between the sheets, the inner sheet being more elastic than the outer sheet to expand greater inwardly toward a supported bag then outwardly when the cuff is inflated;

a gauge to determine and display the pressure within the cuff, the gauge being formed of a housing with a fluid port; and a manifold having a passageway in fluid communication with the cuff, a passageway in fluid communication with a pump for inflating the cuff, and a passageway coupled with respect to the gauge.

4. An apparatus for supporting a flexible bag containing fluid and for applying pressure to the bag to thereby facilitate the dispensing of the fluid from the bag, the apparatus comprising:

a cuff adapted to support a bag of fluid to be dispensed and to apply pressure to facilitate the dispensing of the fluid;

a gauge to determine and display the pressure within the cuff, the gauge being formed of a housing with a fluid port, the gauge including a cylindrical transparent section and a cylindrical, axially shiftable interior member with indicia to be read through the transparent section; and a manifold having a passageway in fluid communication with the cuff, a passageway in fluid communication with a pump for inflating the cuff, and a passageway coupled with respect to the gauge.

5. An apparatus for supporting a flexible bag containing fluid and for applying pressure to the bag to thereby facilitate the dispensing of the fluid from the bag, the apparatus comprising:

an inflatable cuff adapted to support a bag of fluid to be dispensed and to apply pressure to facilitate the dispensing of the fluid;

a gauge to determine and display the pressure within the cuff, the gauge being formed of a housing with a fluid port; and a manifold having a passageway in fluid communication with the cuff, a passageway in fluid communication with a pump for inflating the cuff, and a passageway coupled with respect to the gauge, the manifold being in a configuration having an upwardly extending passageway in fluid communication with the interior of the cuff, a downwardly extending passageway in fluid communication with a squeeze ball for inflating the cuff, an outwardly extending passageway operatively coupled to the gauge and in fluid communication therewith and to assist in the securement of the gauge with respect to the cuff, the manifold also having an additional passageway with a sealing cap coupled by a friction fitting for the quick release of the cap to effect emergency deflation of the cuff.

6. Pressure infuser apparatus for supporting a flexible bag containing fluid and for applying pressure to the bag to thereby facilitate the dispensing of the fluid from the bag, the apparatus comprising, in combination:

a cuff formed of an inner sheet and a superposed outer sheet, each sheet being of a generally rectangular configuration with longer, parallel, horizontal upper and lower edges and with shorter, parallel, vertical side edges extending between the upper and lower edges, the cuff being bendable about a vertical fold line intermediate the side edges, the sheets being fabricated of a flexible fluid-impervious material, all the edges having RF sealed lines around the periphery of the sheets to define an air chamber between the sheets and with additional RF sealed lines coupling the sheets to preclude excess ballooning of the cuff when inflated;

a support plate with a lower extent RF coupled to the sheets adjacent to the upper edge between the fold line and one side edge, the lower extent having a hook coupled to the sheets for supporting a bag, the support plate also having an upper extent with a hole for supporting the cuff;

a strap with a first end RF coupled to the outer sheet adjacent to one side edge and a second end laterally spaced therefrom, the strap being of a length to encompass the cuff when folded with a bag supported interior thereof, pile-type fasteners secured to the first and second ends of the strap for releasably coupling the ends of the strap when supporting a bag;

a gauge to determine and display the pressure within the cuff, the gauge being formed of a housing, the housing having a lower portion with a fluid port adjacent to the bottom thereof, the housing having a central transparent portion, and the housing having an upper portion defining a chamber within the housing, a cup-shaped member located within the chamber, a normally collapsed accordion-shaped member located between the fluid port and the cup-shaped member adapted to expand and raise the cup-shaped member upon the introduction of air into the gauge, a coil spring located between the cup-shaped member against the expansion of the accordion-shaped member, indicia on the surface of the cup-shaped member adapted to be read by an operator through the central portion as a function of the pressure within the cuff as sensed by the gauge, and a support member extending from the upper end of the gauge for coupling to the cuff; and a manifold having an upwardly extending passageway in fluid communication with the interior of the cuff, a downwardly extending passageway in fluid communication with a squeeze ball for inflating the cuff, an outwardly extending passageway with a sealing cap coupled by a friction fitting for the quick release of the cap to effect emergency deflation of the cuff, and a supplemental passageway extending upwardly from the outwardly extending passageway coupled to the accordion-shaped member and in fluid communication therewith and to assist in the securement of the gauge with respect to the cuff.

* * * * *